(12) United States Patent
Baboulaz et al.

(10) Patent No.: US 10,107,747 B2
(45) Date of Patent: Oct. 23, 2018

(54) METHOD, SYSTEM AND COMPUTER PROGRAM FOR DETERMINING A REFLECTANCE DISTRIBUTION FUNCTION OF AN OBJECT

(71) Applicant: Ecole Polytechnique Federale de Lausanne (EPFL), Lausanne (CH)

(72) Inventors: Loic A. Baboulaz, Laussanne (CH); Martin Vetterli, Grandvaux (CH); Paolo Prandoni, Lausanne (CH)

(73) Assignee: Ecole Polytechnique Federale de Lausanne (EPFL) (CH)

( * ) Notice: Subject to any disclaimer, the term of this patent is extended or adjusted under 35 U.S.C. 154(b) by 833 days.

(21) Appl. No.: 13/906,630

(22) Filed: May 31, 2013

(65) Prior Publication Data

US 2014/0354801 A1 Dec. 4, 2014

(51) Int. Cl.
*G01N 21/55* (2014.01)

(52) U.S. Cl.
CPC .................. *G01N 21/55* (2013.01)

(58) Field of Classification Search
CPC ........................................ G01N 21/55
See application file for complete search history.

(56) References Cited

U.S. PATENT DOCUMENTS

| | | | |
|---|---|---|---|
| 6,628,298 B1 * | 9/2003 | Debevec | G06T 15/506 345/632 |
| 7,177,026 B2 | 2/2007 | Perlin | |
| 8,976,256 B2 * | 3/2015 | Hoelscher | H04N 5/2628 348/222.1 |
| 2008/0152215 A1 * | 6/2008 | Horie | G02B 27/2214 382/154 |
| 2008/0180434 A1 * | 7/2008 | Said | H04N 13/0406 345/419 |
| 2008/0304070 A1 | 12/2008 | Bonnet | |
| 2010/0267163 A1 | 10/2010 | Ran et al. | |
| 2012/0200829 A1 | 8/2012 | Bronstein et al. | |
| 2012/0242854 A1 * | 9/2012 | Hoelscher | H04N 5/2628 348/222.1 |
| 2013/0083230 A1 * | 4/2013 | Fukuda | H01L 27/14627 348/340 |
| 2013/0128087 A1 * | 5/2013 | Georgiev | H04N 5/2254 348/307 |
| 2013/0222369 A1 * | 8/2013 | Huston | G06T 17/00 345/419 |
| 2014/0098191 A1 * | 4/2014 | Rime | H04N 5/2254 348/46 |

(Continued)

OTHER PUBLICATIONS

Ward et al., "Irradiance Gradients", Thirsd Eurographics on Rendering Workshop, Bristol, England, May 18-20, 1992.*

(Continued)

*Primary Examiner* — Mohammad J Rahman
(74) *Attorney, Agent, or Firm* — Blank Rome LLP

(57) ABSTRACT

The invention refers to a method for analyzing reflected light of an object. First a light angle distribution for a point of the object is determined. Then a plenoptic projector is controlled to illuminate the point of the object with the determined light angle distribution. Then the reflected light intensity of the point of the object is measured and the measured reflected light is analyzed in dependence of the determined light angle distribution.

6 Claims, 4 Drawing Sheets

(56) References Cited

U.S. PATENT DOCUMENTS

| | | | | |
|---|---|---|---|---|
| 2014/0168395 A1* | 6/2014 | (Wane; Toru | ...... | H04N 13/0406 348/59 |
| 2014/0168401 A1* | 6/2014 | De Bruijn | ............... | G06F 3/013 348/78 |
| 2014/0181630 A1* | 6/2014 | Monney | ............. | G06K 9/00201 715/232 |
| 2014/0232695 A1* | 8/2014 | McGaughan | ......... | G06F 3/0425 345/175 |
| 2014/0239071 A1* | 8/2014 | Hennick | ............ | G06K 7/10732 235/455 |
| 2014/0286566 A1* | 9/2014 | Rhoads | .............. | H04N 13/0275 382/154 |
| 2015/0104074 A1* | 4/2015 | Vondran, Jr. | ............ | G06T 5/002 382/106 |
| 2015/0381908 A1* | 12/2015 | De Bruijn | ............. | G01J 5/0896 348/253 |

OTHER PUBLICATIONS

R. Ramamoorthi, "A Signal-Processing Framework for Forward and Inverse Rendering," Aug. 2002, 207 pages.

S. K. Nayar et al., "Extracting Shape and Reflectance of Lambertian, Specular, and Hybrid Surfaces," Aug. 1988, pp. 1-46.

* cited by examiner

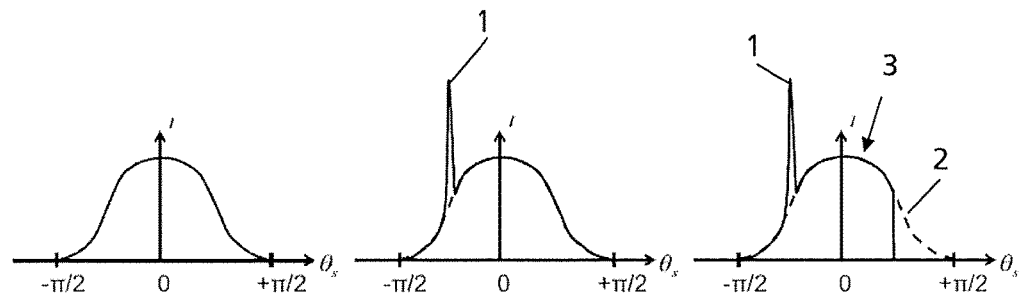
Fig.1A:          Fig.1B:          Fig.1C:
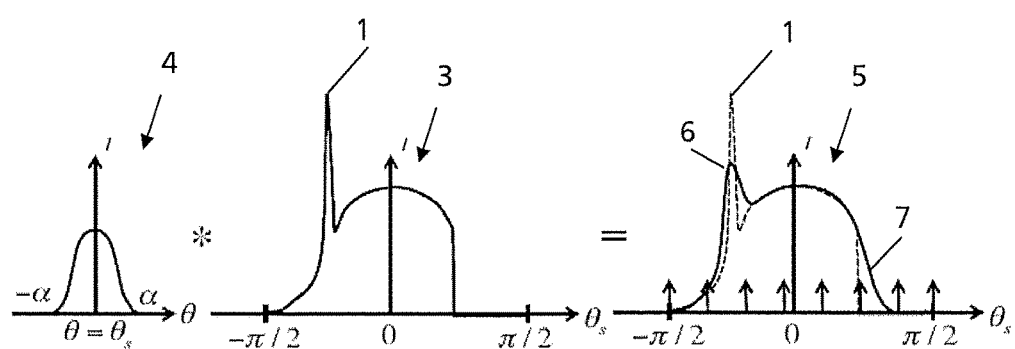
Fig. 2:
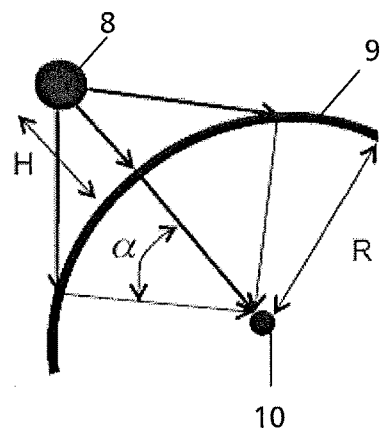 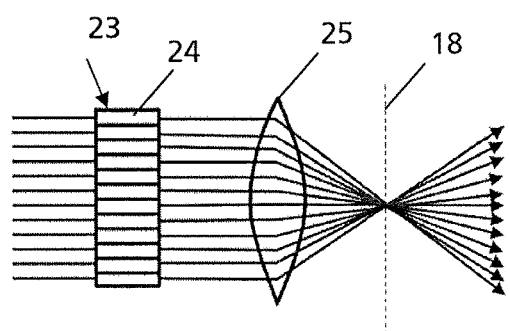
Fig. 3:          Fig. 6:

METHOD, SYSTEM AND COMPUTER PROGRAM FOR DETERMINING A REFLECTANCE DISTRIBUTION FUNCTION OF AN OBJECT

FIELD OF THE INVENTION

The present invention concerns a method, system and computer program for determining a reflectance distribution function of an object.

DESCRIPTION OF RELATED ART

Photos give a realistic representation of an object in the real world. However, photos represent the object only for the given light circumstances and the given direction of observation with respect to the object, when capturing the photo. Therefore, it is desirable to measure the bidirectional reflectance distribution function (BRDF) of each point of the object in order to represent the object for any light circumstances and for any direction of observation.

Once the BRDF of a point of the object is known, the reflected light intensity of this point of the object can be computed by $$L_\lambda(\vec{R}) = \int_{\vec{S} \in S} L_\lambda(\vec{S}) f_\lambda(\vec{S}, \vec{R})(\vec{N} \cdot \vec{S}) d\vec{S}$$

for each set of light sources S and each direction of observation $\vec{R}$ due to the known BRDF $f_\lambda(\vec{S},\vec{R})$. The vector $\vec{N}$ is the surface normal vector at the point of the object and $L_\lambda(\vec{S})$ is the incident light intensity at the point of the object. If the object shall be represented by colours, the BRDF $f_\lambda(\vec{S},\vec{R})$ is dependent on the wavelength λ. In technical applications, a BRDF could be determined for each colour channel (e.g. red, green, blue).

In order to determine the BRDF of a point of an object, the reflectance $f_\lambda(\vec{S},\vec{R})(\vec{N}\cdot\vec{S})$ for each colour value is measured in dependence of the illumination direction of one point light source and in dependence of the observation direction. The two directions ($\vec{S},\vec{R}$) can be parameterized by two incident angles and two reflected angles. Therefore, for each point a reflectance in dependence of four parameters must be measured. This is very time-consuming. In addition, it needs an enormous memory to store all those data.

Therefore, the BRDF is sometimes modelled. FIG. 1A shows a model for the reflectance distribution function of one point at one observation position for a diffuse reflection. FIG. 1B shows such a model for diffuse reflectance with a specular reflection 1 at a specular angle. FIG. 1C shows such a model for diffuse reflectance with a specular reflection 1 at a specular angle and a shadow 3 behind a certain shadow angle. However, it is nevertheless needed to measure the reflectance in order to determine the correct specular angle and correct shadow angle. Since the specular angle is very sharp, a high sampling frequency is needed for the different directions of incident light (illumination direction or angle). Two measured light directions can only have an angle difference smaller than the angle extension of the specular peak 1 in order to assure that the specular peak is measured. Also the shadow angle can only be determined with the exactness of the angle difference of two subsequent measurements.

Therefore, Shree K. Nayar, Katsushi Ikeuchi and Takeo Kanade suggested in the article "Extracting Shape and Reflectance of Lambertian, Specular, and Hybrid Surfaces" to use extended light sources in order to reduce the sampling frequency. FIG. 2 shows a Gaussian distribution for the extended light angle distribution 4 of an extended light source. If a point of an object is illuminated with such an extended light angle distribution 4, the reflectance distribution function 3 of the point of the object is convoluted with the extended light angle distribution 4 resulting in a smoothed reflectance distribution 5. It is seen in FIG. 2 that the power of the specular peak 1 is transported in the angular direction resulting in a reduced intensity peak 6 with a larger full width at half maximum (FWHM) than the specular peak 1. Also the shadow 2 is smoothed in the smoothed shadow area 7. In order to retrieve the reflectance distribution function 3, the reflectance distribution function 3 can be yielded by the deconvolution of the smoothed reflectance distribution 5 with the extended light angle distribution 4.

FIG. 3 shows one embodiment for a light source with a known extended light angle distribution 4. The light source comprises a point light source 8 being arranged at the distance H from a circular light diffuser 9 with radius R. Such a light source would create an extended light angle distribution 4 as shown in FIG. 2. The angle α can be controlled by the parameters H and R. If R is big enough compared to the size of the object, each point on the object has the same extended light angle distribution.

However, such arrangements must be very large in order to guarantee that the light angle distribution at each point of the object is the same. In addition, for each type of extended light angle distribution, another extended light source has to be constructed. Finally, the light source has to be moved for each illumination direction.

BRIEF SUMMARY OF THE INVENTION

The object of the invention is to find a method, system or computer program to analyse reflected light in dependence of the incident light in an easy and simple way.

According to the invention, these aims are achieved by a method, system and computer program for analysing reflected light.

The Method for analysing reflected light of an object, comprises the following steps. A light angle distribution for a point of the object is determined. A plenoptic projector is controlled to illuminate the point of the object with the determined light angle distribution. The reflected light intensity of the point of the object is measured. The measured reflected light is analysed in dependence of the determined light angle distribution.

The system for analysing reflected light of an object comprises a plenoptic projector, a light sensor and a processor. The plenoptic projector comprises a display, a microlense array and a main lense arranged such that the light intensity of a group of pixels of the display is projected by the microlense array and the main lense with different angles at one point of the object. The light sensor is configured to measure the reflected light intensity of the point of the object. The processor is configured to control the light intensity of the group of pixels defining the light angle distribution of the point and for analysing the reflected light in dependence of the light angle distribution.

The computer program is configured to perform the following steps when run on a processor. A light angle distribution for a point of the object is determined. A plenoptic projector is controlled to illuminate the point of the object with the determined light angle distribution. The reflected light intensity of the point of the object is measured. The measured reflected light is analysed in dependence of the determined light angle distribution.

This has the advantage that different illumination angles or different illumination angle distribution can be controlled by the plenoptic projector without the necessity to move the light source. The measured reflected light can be analysed in dependence of every possible light angle distribution being within the range of the plenoptic projector. In addition, the plenoptic projector allows to illuminate not only one point with different light angle distributions, but all points of an area of an object, wherein the light angle distribution of each point can be controlled individually. This reduces the time for necessary measurements enormously.

Further embodiments of the inventions are provided in the dependent claims.

In one embodiment, the determined light angle distribution at the point of the object is a determined extended light angle distribution around one illumination direction. Therefore, the plenoptic projector can be used for the described procedure of determining the BRDF.

In one embodiment, the point of the object is illuminated sequentially from different illumination directions with the determined extended light angle distribution, and the reflectance distribution function at the point of the object at an observation direction is determined by the deconvolution of the measured reflected light distribution over the different illumination directions at the point of the object at the observation direction with the determined extended light angle distribution.

In one embodiment, the plenoptic projector comprises a display, a microlense array and a main lense, wherein each pixel of the display is projected by a microlense of the microlense array and by the main lense with a light angle corresponding to the pixel to a point of the object corresponding to the pixel, and the light intensity of each pixel of a group of pixels of the display corresponding to said point of the object is controlled such that it corresponds to the light intensity of the light angle corresponding to said pixel of the light angle distribution.

In one embodiment, the point is sequentially illuminated at different illumination directions by controlling the group of pixels corresponding to the point such that light is sequentially emitted by different subgroups of this group of pixels.

In one embodiment, the group of pixels illuminating the point are determined on the basis of the relative three-dimensional position of the point to the plenoptic projector.

In one embodiment, the plenoptic projector creates a light angle distribution at each point of at least an area of the object.

In one embodiment, the plenoptic projector creates different light angle distributions at different points of the object.

In one embodiment, the measured reflected light distribution of each point of the object is captured by a photographic camera, especially a plenoptic camera.

In one embodiment, the reflected light intensity of the point of the object is measured by a plenoptic camera.

In one embodiment, the reflected light at different observation directions are measured at the same time with the plenoptic camera, and the reflected light at the point of the object at the different observation angles is analysed in dependence of the determined light angle distribution.

In one embodiment, the plenoptic projector creates a light angle distribution at each point of at least an area of the object, and the reflected light at different observation directions and at each point of the at least one area of the object are measured at the same time with the plenoptic camera, and the reflected light at each point of at least an area of the object at the different observation angles is analysed in dependence of the determined light angle distribution of each point of the at least one area.

In one embodiment, the reflectance distribution function of the point of the object is determined for a number of observation directions, and the bidirectional reflectance distribution function of the point of the object is determined.

In one embodiment, the reflected light intensity of the point of the object at the number of observation directions for each illumination direction is obtained by a plenoptic camera.

In one embodiment, for the observation direction and for the point of the object, at least one of a specular direction and a shadow direction is determined on the basis of the reflectance distribution function of the point of the object and of the observation direction.

In one embodiment, the display of the plenoptic projector is arranged parallel to the microlense array.

In one embodiment, the main lense of the plenoptic projector is arranged in a distance from the microlense array corresponding to the focal length of the main length plus the focal length of the microlenses of the microlense array.

In one embodiment, the computer program comprises the step of receiving data representing the light angle distribution.

In one embodiment, the computer program comprises the steps of creating a signal for creating the light angle distribution of the plenoptic projector at the point of the object, and giving out said signal to the plenoptic projector.

All embodiments can be combined with each other.

BRIEF DESCRIPTION OF THE DRAWINGS

The invention will be better understood with the aid of the description of an embodiment given by way of example and illustrated by the figures, in which:

FIG. 1A shows a first model for the reflectance at one point and at one observation angle for diffuse reflection;

FIG. 1B shows a second model for the reflectance at one point and at one observation angle for diffuse plus specular reflection;

FIG. 1C shows a third model for the reflectance at one point and at one observation angle for diffuse plus specular plus shadowed reflection;

FIG. 2 shows reflected light, when an extended light angle distribution is used for the illumination light;

FIG. 3 shows a first embodiment of a light source with an extended light angle distribution;

FIG. 6 shows the light rays of a group of pixels of a display and of a corresponding microlense of a microlense array of the plenoptic projector;

DETAILED DESCRIPTION OF POSSIBLE EMBODIMENTS OF THE INVENTION

An extended light angle distribution 4 is any distribution not corresponding to a Dirac function. In one embodiment, the extended light angle distribution 4 is a continuous function. In another embodiment, the extended light angle distribution is continuously differentiable. FIG. 2 shows a Gaussian distribution as an example for an extended light angle distribution 4.

Figure 4:
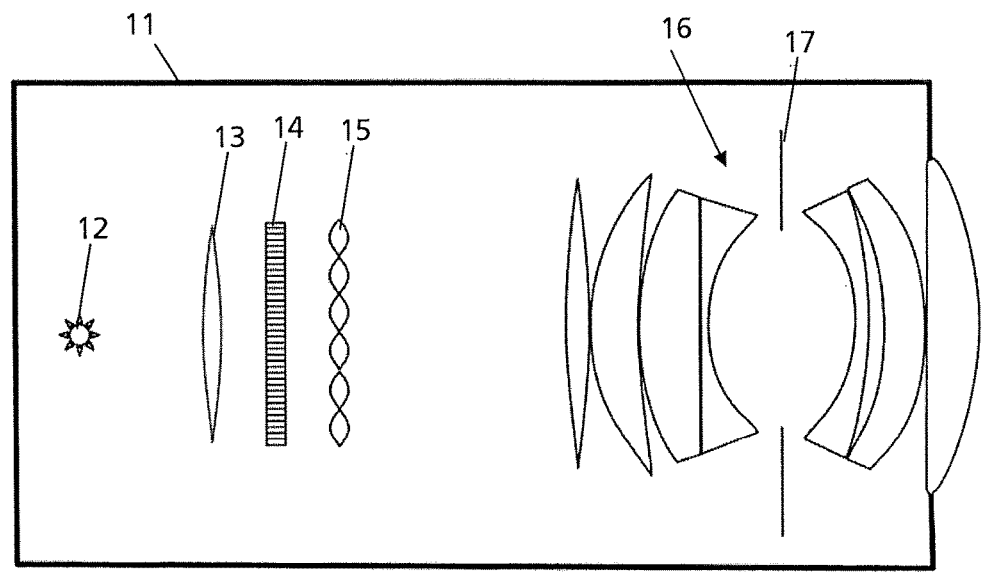
FIG. 4 shows a plenoptic projector as a second embodiment of a light source with an extended light angle distribution.

FIG. 4 shows an embodiment of a plenoptic projector 11. The plenoptic projector 11 comprises a light source 12, a collimating lense 13, a liquid crystal display (LCD) element 14, a microlense array 15, a main lense 16 and an aperture 17. The light source 12, the collimating lense 13 and the LCD element 14 form the display. Instead of an LCD every other display can be used which can control the light intensity of its pixels. Also LCDs with different light sources can be used. E.g. instead of a point light source 12, several light sources, like LEDs can be used.

Figure 5:
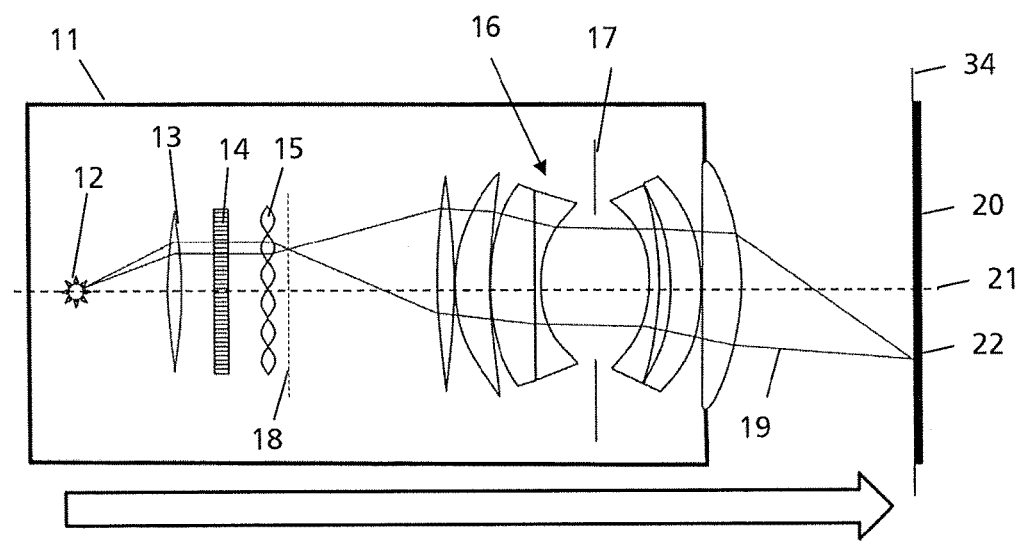
FIG. 5 shows the light rays in the plenoptic projector.

FIG. 5 shows the plenoptic projector 11 projecting light on a surface of an object 20. The light rays 19 relating to one microlense of the microlense array 15 are shown exemplary for all rays of the plenoptic projector 11. The light source 12 emits light. The collimating lense 13 arranged between the light source 12 and the LCD element 14 transforms the radially extending light rays in a bundle of parallel light rays. The parallel bundle of light rays enters the LCD element 14 which is able to control the intensity of the light in each pixel of the LCD element 14. FIG. 6 shows a group 23 of pixels 24 of the LCD element 14 being arranged behind one microlense 25 of the microlense array 15. The group 23 of pixels 24 is defined by the pixels 24 emitting light rays in the direction of the optical axis 21 of the plenoptic projector 11 such that they pass the same microlense 25. As shown in FIG. 6, the light rays of each pixel 24 correspond to another angle of light emitted from the microlense 25. By controlling the intensity of the pixels 24 of one group 23, every possible light angle distribution can be created. Each microlense 25 of the microlense array 15 focuses the light rays of one group 23 of pixels 24 of the LCD element 14 the focal surface 18 of the microlense array 15. After the microlense array 15, the light rays of each microlense 25 are focused by the main lense 16 on one point 22 on the picture surface 34 of the plenoptic projector 11 at the focal length from the main lense 16. Each microlense 25 of the microlense array 15 corresponds to one illuminated point in the picture surface 34. The microarray 15 is arranged in a distance from the main lense 16 corresponding the focal length of the main lense 16 plus the focal length of the microlense array 15 such that the focal surface of the micro lenses 25 and the focal surface of the main lense 16 between the microlense array 15 and the main lense 16 are the same. In FIG. 5, the picture surface 34 corresponds with the surface of the object 20. The light rays being emitted with different angles from the microlense 25 are all focused on point 22. Thus, the group 23 of pixels 24 of the microlense 25 are projected by the main lense 16 to the same point 22 of the picture surface 34, wherein the intensity of the incident light at the point 22 at one of the different incident angles correspond to the intensity of one pixel 24 of the group 23 of pixels 24. Thus, by controlling the intensity of each of those pixels 24 of the group 23, the light angle distribution of this point 22 can be controlled. With the aperture 17, the sharpness of the projected light can be controlled. The light source 12, the collimating lense 13, the LCD element 14, the microlense array 15 and the main lense 16 are arranged in this order on the optical axis 21 of the plenoptic projector 11.

Each microlense 25 of the microlense array 15 corresponds to one point on the picture surface 34. With the group 23 of pixels 24 of the LCD element 14 of each microlense 25 a light angle distribution of the point 22 on the picture surface 34 can be controlled individually for each point 22 and for each light angle. Therefore, the plenoptic projector 11 can illuminate an area with light having at each point 22 a particular light angle distribution. The light angle distribution can be different for each point and can be the same for all points. For the application for measuring the BRDF with extended light sources, the light angle distribution is preferably the same for each of the illuminated points 22.

Possible light angle distributions are a Dirac function (delta function) to create point light sources from one direction, a Gaussian distribution, a step function, an unitary distribution, etc. For the application for measuring the BRDF with extended light sources, preferably, the light angle distribution is symmetric around the angle of incident light. Different light angle distributions can be linearly combined in order to achieve complex light situations.

In FIG. 6, the light angle distribution of the point 22 can be created by using the full range of possible light angles, i.e. by using all possible pixels 24 of the group 23 of one microlense 25. However, a distribution can also be created by only a subgroup of the group 23 of pixels 24 such that the subgroup of pixels 24 defines an extended light angle distribution for one illumination angle and the remaining pixels of the group 23 of pixels 24 block the light. So, the plenoptic projector 11 can illuminate the point 22 of the object 20 sequentially from different angles by using different subgroups of the group 23 of pixels 24 without changing the position of the plenoptic projector 11.

In the embodiment shown in FIG. 5, the surface of the object 20 corresponds to the picture surface 34. Thus, the group 23 of pixels illuminating the same point 22 correspond to all pixels corresponding to one microlense 25. In the case, the point 22 of the object 20 is not in the picture surface 34, the pixels 24 of the LCD element 14 can be controlled with the knowledge of the position of a point 22 on the object 20 such that this point 22 has a desired light angle distribution. Therefore, the pixels 24 corresponding to different microlenses 25 of the microlense array 15 are used to project the light angle distribution on the point 22 of the object 20 being out of focus. This could be used e.g. if a flat object 20 is not arranged rectangular to the optical axis 21 of the plenoptic projector 11 and only one point or one line of the surface of the object 20 would be in the focal length of the main lense 16.

Therefore, the plenoptic projector 11 is a powerful tool in order to control the light angle distribution for one point, selected points or each point of an area of an object 20. The plenoptic projector 11 is well-adapted to project an extended light angle distribution to one point 22 or to several points or to all points of an area of an object 20. However, the plenoptic projector 11 can also be used for illuminating points 22 on the object 20 with a light angle distribution having a Dirac function and varying the incident light angle for this point.

Figure 7:
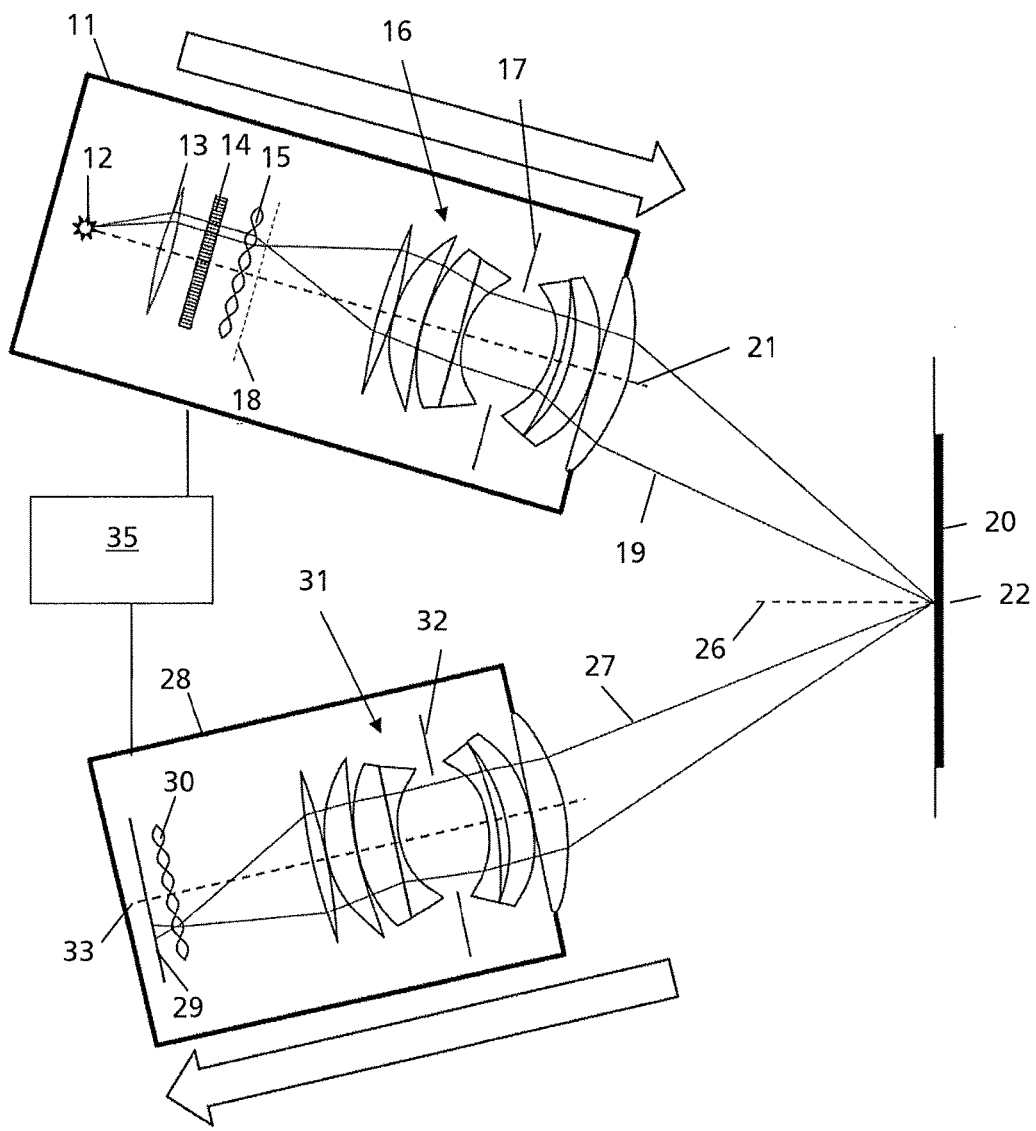
FIG. 7 shows a system for determining the reflectance distribution function of a point of an object.

FIG. 7 shows an embodiment of a system for measuring e.g. the reflectance distribution function of an object 20. The system comprises the plenoptic projector 11, a plenoptic camera 28 and a processor 35.

The plenoptic projector 11 is used as described before to illuminate at least one point 22 of the object 20, preferably each point of an area of the object 20, with an extended light angle distribution 4. The optical axis 21 of the plenoptic projector 11 is arranged at a first angle to the normal 26 of the object 20. The normal 26 of the object 20 is the average normal 26 around the point 22 and not the actual normal at this point. E.g. in the case of paintings, the normal 26 of the surface of the painting would always be rectangular to the painting surface. However, due to the colour on the painting the actual normal at each point is randomly distributed.

The plenoptic camera 28 comprises a charge-coupled device (CCD) sensor 29, a microlense array 30, a main lense 31 and an aperture 32 arranged in this order along the optical axis 33 of the plenoptic camera 28. The microlense array 30 is arranged in the focal distance of the main lense 31 and the CCD 29 is arranged in the focal distance of the microlenses of the microlense array 30. If the point 22 is in the picture surface of the plenoptic camera 28, the intensity of light rays of different angles from point 22 are measured in different pixels of the group of pixels of the CCD 29 being arranged behind one mircrolense of the microlense array 30 corresponding to the point 22. Therefore, the plenoptic camera 28 measures with one shot for all points 22 of an area of the object 20 the reflected light for a number of observation directions. If the point 22 is illuminated by an extended light angle distribution 4, the pixels of the CCD 29 corresponding to the microlense of the microlense array 30 corresponding to point 22 measures the reflected light from point 22 for a plurality of observation angles. The measurement is repeated for each illumination angle. In this embodiment, a plenoptic camera 28 is used as light sensor for the reflected light of point 22, because a plurality of observation angles and a plurality of points 22 can be measured at the same time with one measurement.

The combination of the plenoptic projector 11 and the plenoptic camera 28 allows to control the complete light path from the light source, over the object to the light sensor. Such an arrangement allows to measure a huge number of settings (different incident light angle distributions for each point of the object and different observation angles for all illuminated points) without moving the plenoptic projector 11 or the plenoptic camera 28 or the object. The combination is very advantageous for measuring the BRDF with extended light sources. However, the invention is applicable for each measurement which wants to analyse reflected light in dependence of a particular incident light angle distribution. However, the invention is not restricted to plenoptic cameras 28 as light sensors. A simple photo camera or another light sensor could be used instead.

The processor 35 is configured to control the LCD element 14 of the plenoptic projector 11 such that at point 22 or at selected points or at each point of an area of the object 20 a specific extended light angle distribution is projected. The processor 35 is further configured to control the angle of the incident light (illumination angle/direction) at point 22 or at selected points or at each point of an area of the object 20. This can be performed by changing a subgroup of pixels 24 of a group 23 of pixels 24 wherein the group 23 of pixels 24 project each light on the same point 22 of the object 20. Alternatively, this can be performed by moving the plenoptic projector 11, i.e. by changing the angle of the optical axis 21 compared to the surface normal 26 of the object. The processor 35 is configured to receive the measured reflected light of the CCD 39. The processor 35 is further configured to calculate the reflected light intensity of all points of the area of the object 20 being covered by the plenoptic camera 28 for all observation directions covered by the angle range of the plenoptic camera 28. The processor 35 is further configured to provide for each point and for each observation angle a reflectance function from the measured reflected light over different illumination angles. The processor 35 is further configured to compute a reflectance distribution function at point 22 at the observation angle by the deconvolution of the extended light angle distribution at point 22 and the measured reflected light over different illumination angles. The processor 35 is further configured to analyse the measured reflected light of point 22 or of all points of an area of the object 20 on the basis of the light angle distribution (extended or delta function) of the plenoptic projector 11.

Figure 8:
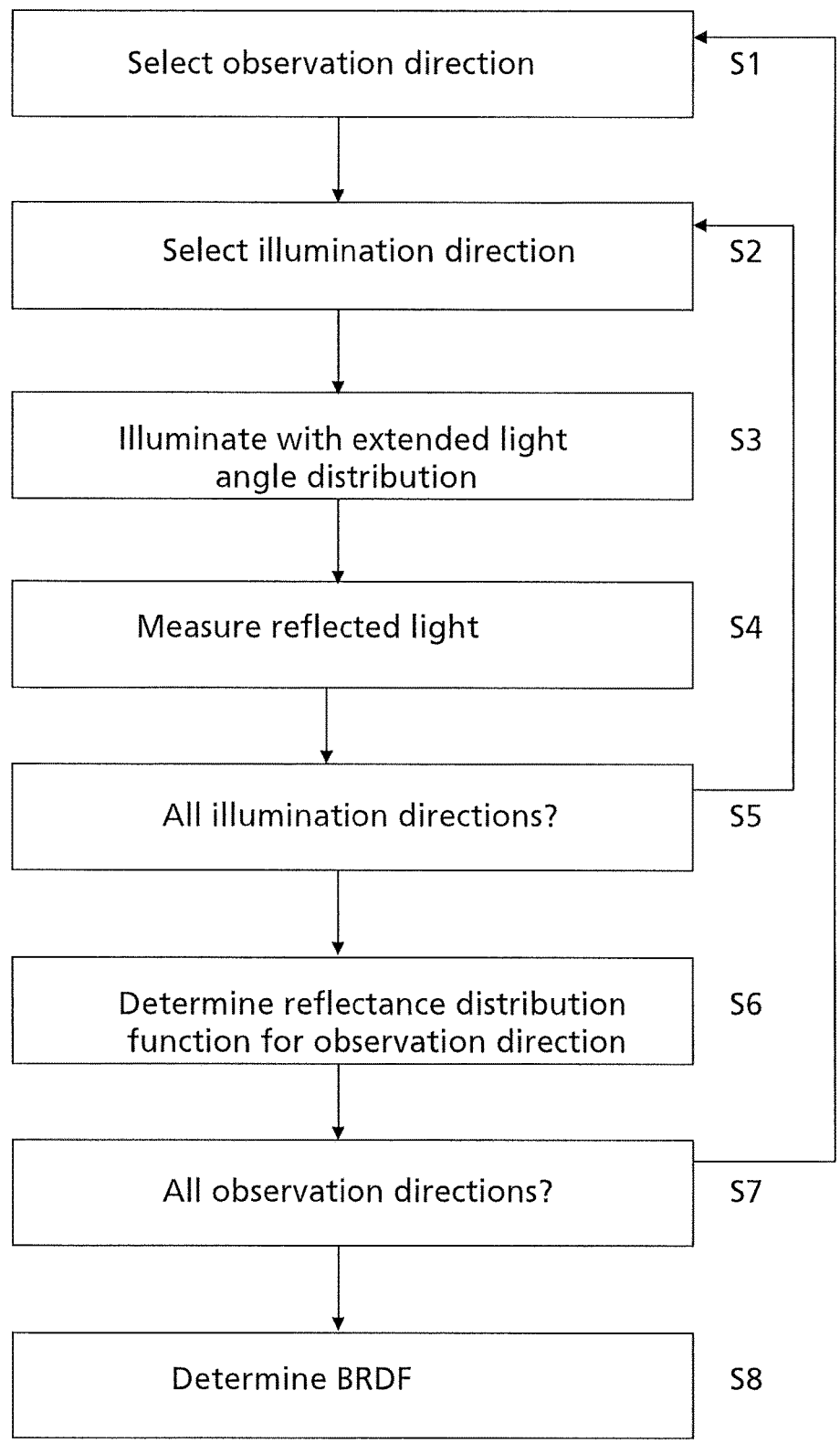
FIG. 8 shows a method for determining the reflectance distribution function of a point of an object.

FIG. 8 shows an embodiment of a method to measure the reflectance distribution function for the point 22 or for each point of an area of an object 20 and to determine the BRDF at the point 22 or for each point of an area of an object 20.

In step S1 an observation direction is selected. In the embodiment of FIG. 7, several observation directions being measured by the plenoptic camera 28 are selected at the same time. If the plenoptic camera 28 is very close to the object 20, the range of observation directions measured by the plenoptic camera 28 in one position might be enough for determining a BRDF. Otherwise, the plenoptic camera 28 can be moved in order to increase the measured observation angle range. In step S1, one of the observation angles measured in the plenoptic camera 28 is chosen. In step S2, an illumination direction is selected. The illumination direction can either be controlled by moving the light source or by controlling the light angles of the light source, e.g. by controlling the LCD element 14 of the plenoptic projector 11, or by a combination of both. If the plenoptic projector 11 is very close to the object 20, the angle range of the plenoptic projector 11 might be enough to illuminate the point 22 at sufficient different illumination angles to create a measured reflectance distribution over the illumination angles. Alternatively, the illumination projector 11 can be moved in order to obtain different illumination angles. Alternatively, both methods can be combined and at each position of the plenoptic projector 11, illumination under several illumination angles can be performed by using only subgroups of one group 23. In step S3, the point 22 or all points of an area of the object 20 is illuminated with an extended light angle distribution 4 from the selected illumination direction. Therefore, the processor 35 controls the plenoptic projector 11 such that the point 22 or all points of an area of the object 20 is or are illuminated with the extended light angle distribution 4. Preferably, each point is illuminated with the same extended light angle distribution 4. In step S4, the light reflected from point 22 or from all points of the area of the object 20 is measured by the plenoptic camera 28 under the selected observation direction. The processor 35 stores the measured reflected light intensity. In step S5, it is determined, if all desired illumination directions have been measured? If no, the steps S2 to S5 are repeated for the remaining illumination directions. If yes, in step S6, the reflectance distribution function for the selected observation direction is determined by the deconvolution of the measured reflected light at point 22 over the different illumination angles and the extended light angle distribution 4 used for each illumination direction. The extended light angle distribution 4 for different illumination angles must be always the same at least for the same point 22. In step S7, it is checked, if the reflectance distribution function has been determined for all observation directions. If no, the steps S1 to S7 are repeated for the remaining observation directions. In the case, that different observation directions are measured at the same time with the plenoptic camera 28 or with several plenoptic cameras 28 or with several photographic cameras, only step S1, S6 and S7 have to be repeated, since the data of the reflected light intensity for this illumination direction has already been measured and stored. If the plenoptic camera 28 or any other light sensor is moved to another position, the steps S1 to S7 have to be performed again. If the reflectance distribution function is determined for all observation directions, the reflectance distribution function of all observation directions are combined to receive the BRDF in step S8.

FIG. 8 shows only one embodiment of the method of analysing reflected light. Instead of extended light angle distributions also dirac light angle distributions can be used. Instead of a BRDF, any other function of the measured reflected light can be computed in dependence of the incident light angle distribution.

The invention was shown in the figures for simplicity only in a two-dimensional scenario. However, it is understood that every step can also be performed in a three-dimensional scenario. The invention is not restricted to the shown and described embodiments, but includes all embodiments falling under the protection of the independent claims.

The invention claimed is:

1. A method for analysing reflected light of an object, comprising the steps of:
   determining in a processor a light angle distribution for a point of the object;
   illuminating with a plenoptic projector the point of the object with the determined light angle distribution such that a bidirectional reflectance distribution function of the point of the object is convoluted with the extended light angle distribution resulting in a smoothed bidirectional reflectance distribution of the point of the object;
   measuring with a light sensor for a plurality of observation angles the light intensity of the point of the object reflecting the light angle distribution of the plenoptic projector for measuring the smoothed bidirectional reflectance distribution of the point of the object;
   determining in the processor the bidirectional reflectance distribution function on the basis of the deconvolution of the measured reflected light intensity for the plurality of observation angles of the point of the object and the determined light angle distribution,
   determining at least one of a specular direction and a shadow direction of the point of the object on the basis of the determined bidirectional reflectance distribution function of the point of the object.

2. The method according to claim 1, wherein the plenoptic projector comprises a display, a microlense array and a main lense, wherein each pixel of the display is projected by a microlense of the microlense array and by the main lense with a light angle corresponding to the pixel to a point of the object corresponding to the pixel, and the light intensity of each pixel of a group of pixels of the display corresponding to said point of the object is controlled such that it corresponds to the light intensity of the light angle corresponding to said pixel of the light angle distribution.

3. A system for analysing reflected light of an object, comprising:
   a plenoptic projector comprising a display, a microlense array and a main lense arranged such that each pixel of the display is projected by a microlense of the microlense array and by the main lense with a light angle corresponding to the pixel to a point of the object corresponding to the pixel;
   a light sensor for measuring the light intensity of the point of the object reflecting the light angle distribution of the plenoptic projector for a plurality of observation angles;
   a processor
      for controlling the light intensity of each pixel of a group of pixels of the display corresponding to a point of the object such that it corresponds to the light intensity of the light angle corresponding to said pixel of a determined light angle distribution such that a bidirectional reflectance distribution function of the point of the object is convoluted with the extended light angle distribution resulting in a smoothed bidirectional reflectance distribution of the point of the object; and
      for determining a bidirectional reflectance distribution function on the basis of the deconvolution of the measured reflected light intensity of the point of the object for a plurality of observation angles and the determined light angle distribution.

4. The according to claim 3, wherein the determined light angle distribution at the point of the object is a determined extended light angle distribution around one illumination direction.

5. The system according to claim 3, wherein the processor is further configured for determining at least one of a specular direction and a shadow direction of the point of the object on the basis of the determined bidirectional reflectance distribution function of the point of the object.

6. The system according to claim 5, wherein the processor is further configured to determine the at least one of a specular direction and a shadow direction of the point of the object for each of the plurality of observation directions.

* * * * *